United States Patent [19]

Gore

[11] Patent Number: 4,918,981

[45] Date of Patent: Apr. 24, 1990

[54] METHOD FOR MEASURING MOISTURE VAPOR TRANSMISSION RATE IN WEARING APPAREL

[75] Inventor: Robert W. Gore, Newark, Del.

[73] Assignee: W. L. Gore & Associates, Inc., Newark, Del.

[21] Appl. No.: 263,931

[22] Filed: Oct. 28, 1988

[51] Int. Cl.$^5$ .............................. G01M 3/26
[52] U.S. Cl. .................... 73/76; 2/DIG. 7; 73/38; 177/25.14
[58] Field of Search ............... 73/38, 45.5, 76; 2/DIG. 7; 177/25.14

[56] References Cited

U.S. PATENT DOCUMENTS

| | | | |
|---|---|---|---|
| 2,054,204 | 9/1936 | McDonald | 73/45.5 |
| 2,874,566 | 2/1959 | Mastak | 73/38 X |
| 3,116,629 | 1/1964 | Neil | 73/38 |
| 3,166,439 | 1/1965 | Dennhofer | 73/45.5 |
| 4,194,041 | 6/1978 | Gore | |
| 4,344,999 | 8/1982 | Gohlke | 2/DIG. 7 X |
| 4,550,446 | 11/1985 | Herman | 2/239 |
| 4,799,384 | 1/1989 | Casali | 73/45.5 |
| 4,838,705 | 6/1989 | Byers, Jr. et al. | 73/76 X |

OTHER PUBLICATIONS

ASTM E 96-80, Standard Text Method for Water Vapor Transmission of Materials, approved Oct. 31, 1980, originally E 96-53t and last edition t96-66 (1972), (pp. 795-804).

Primary Examiner—Daniel M. Yasich
Attorney, Agent, or Firm—Gary A. Samuels

[57] ABSTRACT

A method and apparatus for testing wearing apparel that defines an enclosure for moisture vapor transmission. Thin, flexible, waterproof liners which have a high permeability to moisture vapor are inserted into the interior of the apparel and filled with water. The water may be heated to simulate body temperatures and to produce higher concentrations of moisture vapor inside the apparel article. The amount of moisture transferred to the external environment of the apparel article, as well as the amount of moisture absorbed and condensed in the apparel article itself, can be measured by the weight differences which occur over a test period. The method is non-destructive and suitable for quality control, as well as for new product design.

3 Claims, 3 Drawing Sheets

METHOD FOR MEASURING MOISTURE VAPOR TRANSMISSION RATE IN WEARING APPAREL

FIELD OF THE INVENTION

This invention relates to a method for measuring the moisture vapor transmission rate of wearing apparel.

BACKGROUND OF THE INVENTION

Comfortable wearing apparel allows moisture which is naturally evaporating from the skin to dissipate so there is never a buildup of high humidity or liquid moisture near the skin area. Failure of the apparel to allow this moisture to dissipate causes the body to feel hot and uncomfortable in the area the apparel covers. The dissipation of moisture vapor can occur in a number of ways: into the ambient air through openings in the apparel; into ambient air through the materials making up the apparel, or in the case of leather, a limited amount of moisture vapor can be absorbed spontaneously within the leather to reduce humidity buildup.

There are methods of measuring the rate of moisture transmission and absorption of wearing apparel, but wearing apparel such as footwear, gloves and hats are not ordinarily, easily and inexpensively tested for their moisture vapor transmission properties. This is especially true of footwear, such as, shoes and boots. For most shoes and boots, perhaps the most important mechanism for dissipating humidity in the microclimate near the foot is diffusion of moisture vapor from the inside of the shoe, through the shoe materials, to the external environment. There has not been an easy, inexpensive way to measure these properties of a finished shoe or boot. While actual wear tests by human subjects can be used to determine the comfort level of a shoe, such tests require a strict test protocol for accurate results, are time-consuming to perform, and are consequently expensive. The materials used in manufacturing shoes can presently be tested for their ability to transmit moisture through them by a variety of techniques, one of which is ASTM-E96-B 66B, and another method which can be used for waterproof materials only is described in U.S. Pat. No. 4,194,041 at column 7 lines 28 through 48. These methods are useful for determining the moisture vapor transmission rate (MVTR) of materials available in sheet form such as leather and shoe fabric. However, in the construction of a footwear article, these materials are stretched or deformed into other shapes. Such deformation processes can affect the MVTR by changing the microstructure of the materials as well as by changing the thickness and shape. There is also concern about the deleterious effect adhesives used in footwear construction may have, since most adhesives have low MTVR when tested as a coherent film of adhesive. Also, it would seem that the overall MVTR of a shoe would be adversely affected by the bits and pieces of very low MVTR materials that are often used, such as plastic or metal heel and toe supports as well as certain decorative pieces. Even given the exact knowledge of the geometry, position, and MVTR of each component in a shoe, it is not obvious how to calculate what the overall rate of moisture transmission from the shoe will be. A method for measuring the moisture transmitted through a finished shoe is of great value; especially when such a method is non-destructive to the footwear article so that it can be used for manufacturing quality control; especially when the test apparatus is not expensive; and, especially when the method yields repeatable quantitative results that correlates with footwear comfort.

BRIEF DESCRIPTION OF INVENTION

The invention described here provides a repeatable method of measuring the relative MVTR of wearing apparel that defines an enclosure, especially articles of footwear or gloves, as well as providing good absolute measures of MVTR. In this invention, a thin, waterproof, flexible material having a very high MVTR is inserted as a loose waterproof lining into the interior of the apparel to be tested so that the lined interior can be filled with water. The waterproof lining material must be flexible and thin enough so that the water presses it to conform snugly to the interior contours of the apparel, whether the apparel is footwear, gloves or hats, or the like. A plug, which is impervious to liquid water and water vapor, is clamped into the entry passage in the interior of the apparel to prevent water from evaporating through the passage. This plug can be made to accommodate and support heating elements and temperature probes. Water is lost by evaporation through the liner, which is vapor permeable but liquid water impermeable. All water lost through the liner must either be absorbed in the apparel or permeate entirely through the walls of the apparel into the external environment. Thus, by weighing the water-filled apparel before and after a test period, the weight of water lost to the environment during the period can be determined. The apparel itself can also be weighed before and after the test period to find out how much water it has absorbed. These two weights should sum up to the total weight of water lost from the initial reservoir of water contained within the liner. An independent check of the total water lost from the reservoir of water can be made by weighing the water actually added to the reservoir prior to starting the test and comparing this with what remains in the liner after the test period.

DETAILED DESCRIPTION OF THE INVENTION

Figure 1:
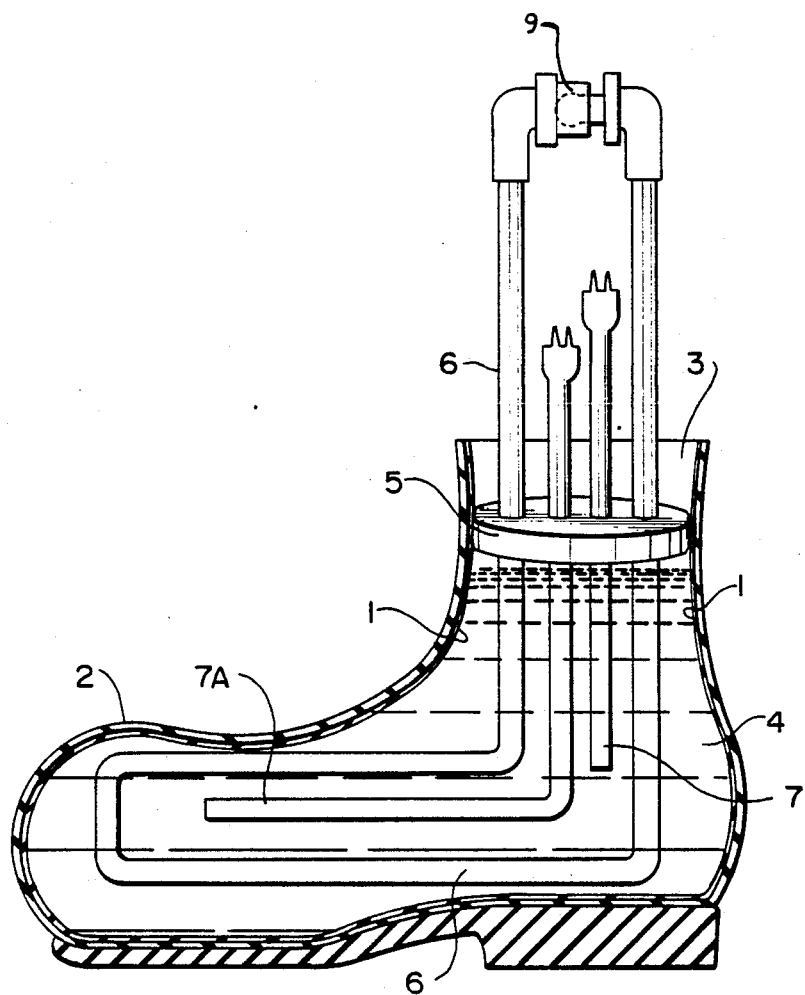
FIG. 1 is a schematic partially three dimensional view of one test apparatus used in the invention.

While the test procedure of this invention is useful in determining the MVTR of any wearing apparel that defines an enclosed area, such as hats, gloves, socks, boots, shoes, and the like, it is particularly useful with footwear, such as boots or shoes. Accordingly, in the ensuing discussion reference will be made to footwear throughout with the understanding that the discussion is applicable to other types of wearing apparel.

The term "moisture vapor transmission rate" (MVTR) is used here as a general term that also includes specific measurement techniques. In all measurement techniques to determine MVTR, however, water vapor moves by diffusion caused by concentration differences of water vapor. The amount of water vapor transmitted will depend on the magnitudes of (1) the concentration differences, (2) the resistances, (3) the time allowed for transmission to occur, and (4) the area through which transmission is occurring. Each of these four general variables needs considerable detailing to lead to a standard, repeatable test for MVTR. The driving force for diffusion of vapor through a footwear article is the difference in concentration of moisture vapor between the interior and the external environment. The concentration of water vapor at the liner will be very sensitive to the temperature of the water inside the footwear. Usually footwear articles are tested in an environment of air, and in this case the concentration of vapor in the environmental air can be determined by measuring the humidity by standard techniques such as a wet/dry bulb thermometer. In some situations, water vapor may condense in a footwear article and wicking may occur. In this case, water is not transported by diffusion alone and a decision must be made whether this is a realistic situation in the intended use of the footwear article. One situation which leads to condensation of the water vapor leaving the liner is high water vapor driving force in footwear articles with high resistance to moisture vapor diffusion. Another situation arises when testing in cold external environments, especially when the footwear article is insulated with a poor insulating material, i.e. an insulating material that has a relatively high thermal conductivity combined with a relatively high resistance to moisture vapor diffusion. Techniques for lowering the water vapor concentration driving force to prevent condensation include lowering the water temperature in the reservoir or filling the reservoir with a water-salt solution. Various salts can be selected to lower the water vapor pressure considerably while still allowing the footwear interior to be maintained at body temperature or at expected foot temperature. Rather, much of the merit of this invention is the wide applicability and usefulness in evaluating different kinds of footwear under various environmental conditions. The process steps of the invention will now be described with reference to FIG. 1. The steps comprise, in sequence:

(a) inserting into wearing apparel product 2, a water vapor permeable, liquid waterproof liner material 1 which is adaptable to fit and line the interior of wearing apparel product 2, and to abut sealing plug 5 preferably by protruding through hole 3 into the space outside the apparel product, (b) filling the liner material with a quantity of water 4, and plugging and sealing said hole 3 with a sealing plug 5 that is impervious to both liquid water and water vapor, such as Plexiglass, such that a water and vapor seal is formed, (c) weighing said sealed water-filled wearing apparel product 2, (d) allowing the sealed water-filled wearing apparel product 2 to set for a predetermined time, (e) reweighing said sealed water-filled wearing apparel product, and (f) determining the transmission rate of water vapor passing through the wearing apparel product.

The water inside liner material 1 can be heated if desired by various means, for example, inserting tubing 6 inside the liner material 1 and passing heated water through it. The water temperature can be measured by thermocouples 7 and 7A which monitor water temperature in the center 7 and near the toe, 7A. Element 9 in FIG. 1 is a "Quick-Fit" connector. Such a connector is well known in the art and is made of two plastic pieces that fit together to seal off the heated water in tub 6 and make it a closed system.

Rather than making a lining that precisely fits the interior shape of the boot, it is less expensive, and much more versatile to choose liner material that can function by taking the shape of the boot even though it is in the form of a flat sheet or an oversized foot shape where one size fits all footwear. For this embodiment of the invention, the liner material must be flexible so that it can be inserted into the footwear and conform to the interior contours; it must be thin, so that the folds that form do not create increases in thickness that substantially change the interior size and shape of the footwear product; it must have much higher MVTR than the footwear product to be tested; and it must be waterproof so that only moisture vapor contacts the interior of the footwear product rather than liquid water. A number of commercially available materials are suitable for the liner material. These materials include microporous expanded polytetrafluoroethylene (PTFE) such as is described in U.S. Pat. Nos. 3,953,566 and 4,187,390; expanded PTFE coated with hydrophilic impregnants and layers, such as is described in U.S. Pat. No. 4,194,041; breathable polyurethane films; or elastomers, such as copolyetheresters and laminates thereof described in U.S. Pat. No. 4,725,481 and 4,493,870.

While the technique of this invention is particularly suitable for wearing apparel that has only one opening such as footwear, headwear, armwear or handwear, it can be used with trousers, shirts, or coats and the like with suitable adaptation to take into consideration the several openings of such garments.

EXAMPLES

EXAMPLE 1

Figure 2:
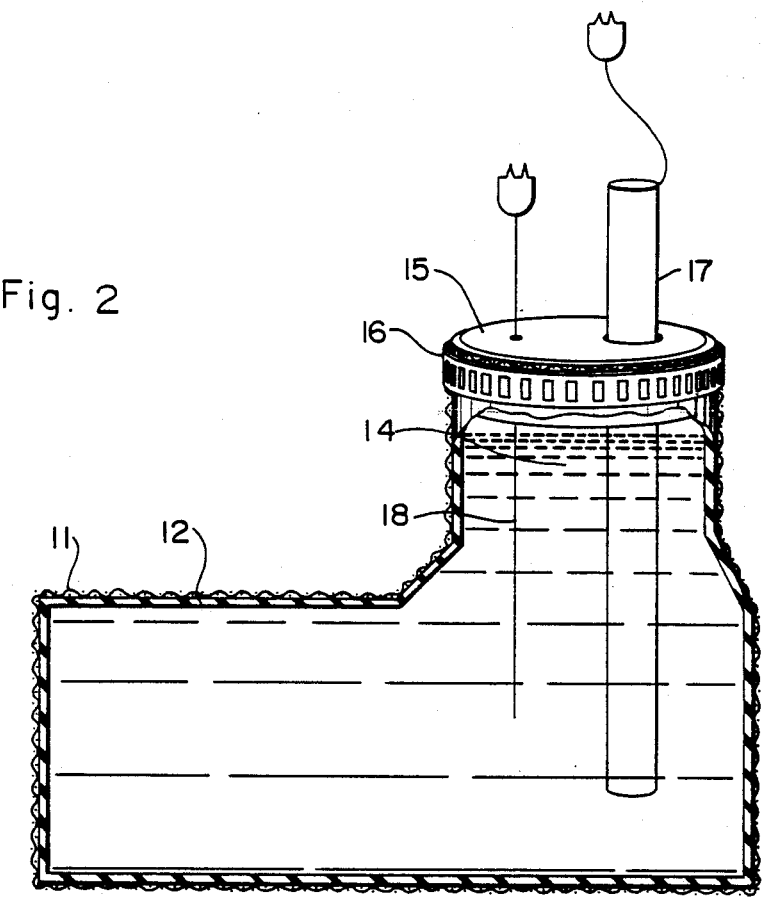
FIG. 2 is a schematic partially three dimensional view of another test apparatus used in the invention.

Referring to FIG. 2, normal window screen made up of wires of about 0.01 inch diameter on 0.05 inch centers was fabricated into the size and shape of a hiking boot 11. The purpose of this screen boot was to contain and support a thin, flexible liner film 12 while still allowing great exposure of the film surface to the ambient air, i.e. to support, while not obstructing or interfering with moisture-vapor transport through the film. A film of expanded PTFE, manufactured according to the teachings of the U.S. Pat. No. 3,953,566 and obtainable as GORE-TEX ® waterproof, vapor-permeable material from H. L. Gore & Associates was fitted into the interior of the screen boot allowing the flat film to wrinkle and fold as it generally accomodated to the interior shape. The film was about 0.004 inch thick and had a porosity of about 75%. Such films can be tested for their own MVTR according to the procedure set forth in column 7, lines 28–48 of U.S. Pat. No. 4,194,041. This procedure is as follows:

Approximately 80cc of water is placed in a tapered polypropylene cup which is 4.5 inches high with a 2.5" diameter mouth. The material to be tested is sealed to the lip of the cup with a silicone adhesive. The cup assembly is weighed to the nearest 1/100 gram and an elastic rubber collar is placed on the cup under tension. In an environmental chamber, the assembly is suspended upside down through a circular opening in a support plate, its position being adjusted by means of the rubber collar so that the mouth of the cup is aligned with the lower surface of the plate.

Between this surface and the bottom of the chamber, there is an approximately 4" air space across which air is caused to flow at about 650 ft/min. The chamber is held at a temperature of 73°±2° F. and a relative humidity of 50%±2%. The sample remains in the chamber for three hours and is then removed and weighed again to within 1/100 of a gram. The moisture vapor rate is then expressed in grams of water lost per square meter of sample surface area per 24 hours.

Water was added through the leg-hole 14 into the waterproof reservoir created and provided by the film 12. The leg-hole 14 was sealed off with plug 15 and held to the screen boot and liner film with hose clamp 16. The water was heated with a fish-tank heater 17 and water temperature was monitored with thermocouple 18.

The entire apparatus was weighed and then suspended from a wire so that air could circulate freely on all sides and this air circulation was aided with a fan which produced a light breeze about five miles per hour. The air temperature was about 70° F. and humidity about 60%. Water inside the boot was maintained at about 37° C. in the area of the thermocouple. The water temperature was cooler below this position and warmer above due to the natural buoyancy of warmer water.

Water was allowed to evaporate for four hours, and then the entire apparatus was reweighed. The moisture-vapor transmission rate (MVTR) for the screen boot (MVTR) was calculated as follows:

$$MVTR = \frac{\text{Total water weight in grams lost by apparatus}}{\text{Duration of test in hours}} = 45 \text{ g/hr}$$

The value of 45 g/hr is the upper limit of MVTR for this apparatus under these test conditions, since the screen boot provides very little resistance to moisture transfer. So long as the measured MVTR of real boots is well below this value, it is to be expected that the expanded PTFE waterproof, vapor-permeable liner is not affecting the measured result and that we are measuring the MVTR of the boot itself.

EXAMPLE 2

A boot deemed by a sensitive wearer as very comfortable was tested by the method of Example 1. The boot was substituted for the screen boot of Example 1. The boot was first weighed and then a liner inserted as in Example 1. Water was added, and the product was weighed again. After seven hours of testing under the conditions of Example 1, the boot was reweighed to determine the total amount of water that had evaporated from the boot assembly during the test. Then, all of the remaining water was emptied from the liner, and all apparatus was removed from the boot and the boot itself was weighed, and this weight compared to initial boot weight to determine how much moisture, if any, had been condensed in the boot or absorbed by the boot. The absorbed water was present due to temperature induced condensation of water vapor and also by absorption of water vapor into the component materials of the boot. The results showed 66.8 g absorption. The boot's MVTR was calculated to be 10.99 g/hr.

Comparison Example—Uncomfortable Boot

An all rubber insulated boot was worn by the same person who wore the comfortable boot in Example 2. The rubber boot was deemed to be very hot and uncomfortable. The rubber boot was tested in the same manner as described in Example 2. The results showed absorption and condensation in the rubber boot of 17.4 g.

The boot had an MVTR of 0.3 g/hr. For the above examples it can be seen that both comfortable and uncomfortable boots have MVTR values below the upper limiting value of the test apparatus as determined in Example 1, and further that this test procedure distinguishes clearly between comfortable and uncomfortable boots with regard to MVTR.

EXAMPLE 3:

Using the apparatus of FIG. 1, the water is heated by circulating water through copper tubing 6. Heat is thus supplied throughout the water in the boot and especially down to the toe region. Thermocouple 7 and 7A to monitor water temperature. Quick connectors 9 provide for easy connect/disconnect of the copper tubing to a constant temperature water source.

An insulated hunting boot was weighed and then tested by the assembly shown in FIG. 1. Water was added to the liner inside the boot, and the assembly sealed off and weighed. The test was run for 26 hours in a controlled environment of 23° C. and 50% relative humidity. The water in the liner was maintained at 35° C. After the test, the assembly was reweighed for MVTR calculation, and the boot alone was reweighed for the absorption calculation.

Results:

MVTR—Hunting Boot—Water Test=2.1 g/hr
Absorption and Condensation—Hunting Boot—Pure Water in Reservoir Test=140 g (liquid water poured out of boot after test)

The inside of the hunting boot was very wet after the test. The water vapor pressure difference in the test is 42.2 mbar. The calculation is as follows:

---

56.2 mbar (at 100% RH, 35° C.)
−14.0 mbar (at 50% RH, 23° C.)
42.2 mbar = Water Vapor Pressure Difference for Water Test

---

To reduce condensation inside the boot, the vapor pressure difference in the test was reduced. In addition to reducing the vapor pressure by reducing the temperature inside the liner, the relative humidity inside the liner was further reduced by using a saturated salt solution inside the liner instead of pure water. There are any number of combinations of salt solutions and temperatures that can be chosen for liner environment. In this example, excess sodium chloride was added to water to form a saturated salt solution which was then added to the reservoir in the boot. The solution created a relative humidity of about 76% at test temperature. Test temperature was about 28° C. The room conditions were unchanged, and the same boot was tested. The water vapor pressure difference test is 14.7 mbar as calculated below:

---

28.7 mbar (at 76% RH, 28° C.)
14.0 mbar (at 50% RH, 23° C.)
14.7 mbar = Water Vapor Pressure Difference for Salt Test

---

Results:

MVTR for Hunting Boot using saturated salt solution=0.2 g/hr.
Absorption and condensation in Hunting Boot in Salt Test=1.0 g (boot felt dry inside after test)

These results show that different relative humidities and temperatures can be created inside the liner to develop a test that causes less condensation inside the boot. Ambient humidity and temperature could have been altered for a similar effect.

EXAMPLE 4

Figure 3:
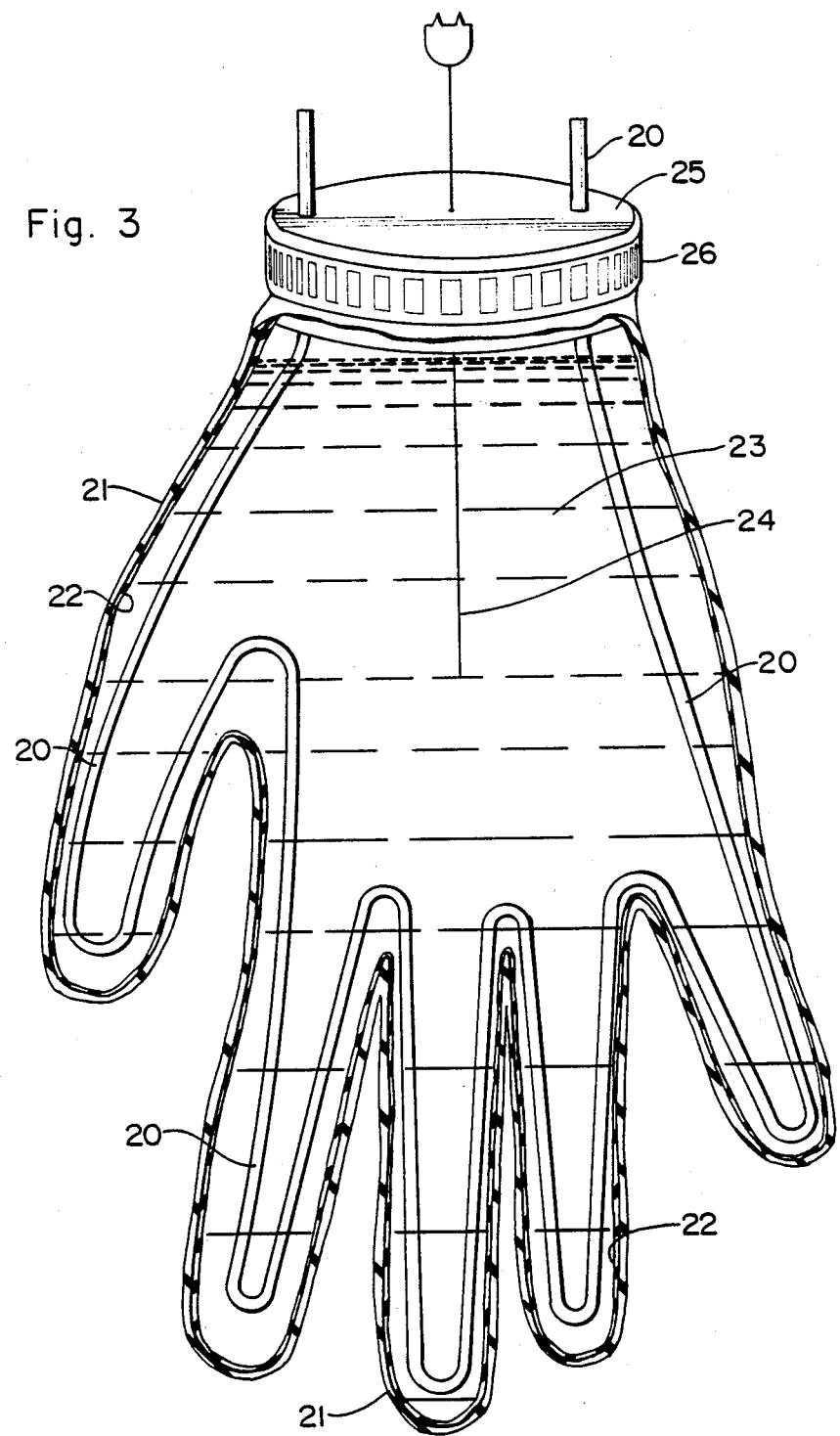
FIG. 3 is a schematic cutaway view of a test apparatus for gloves with a waterproof liner inside.

A ski glove was tested for MVTR with an apparatus and procedure similar to that already been described for footwear, but modified to the geometry of the glove, as is shown in FIG. 3. A copper tube 20 was bent to the shape of a hand so that it would extend into the fingers of the glove 21. A flat sheet of expanded PTFE film could not be used easily, since it was difficult to form it and insert it into the glove without undue folding and buildup of wrinkles in the fingers. An insert 22 was therefore made in the shape of a glove from two films of expanded PTFE. The films were thermally bonded with the aid of an adhesive. This insert could easily be put into the position shown. The glove insert was then filled with water 23, the copper tube 20 was inserted along with thermocouple 24 and plug 25. Clamp 26 was tightened to hold the glove 21 and glove insert 22 against rigid plug 25. The weighing procedures were similar to the previous examples.

A two hour test was run with ambient conditions of 23° C. and 50% relative humidity. Water temperature was 33° C.

Results:

MVTR of Glove in Water = 9.3 g/hr
Absorption and condensation in Glove in Water = 4.8 g

I claim:
1. A method for measuring the moisture vapor transmission rate of a wearing apparel product having an opening, comprising in sequence,
   (a) inserting through said opening into the wearing apparel product a water-vapor-permeable, liquid-waterproof liner material which is adaptable to fit the shape of the wearing apparel and line the inner surface of the product, such insertion being in a manner which allows the liner material to abut a sealing plug defined in step (b),
   (b) filling the liner material with a quantity of water by pouring water through the opening, and plugging and sealing said opening with said sealing plug that is impervious to both liquid water and water vapor, such that a water and vapor seal is formed,
   (c) weighing said sealed water-filled wearing apparel product,
   (d) allowing the sealed water-filled wearing apparel product to set for a predetermined time,
   (e) reweighing said sealed water-filled wearing apparel product, and
   (f) determining by calculating, from the weighting and the reweighing steps the transmission rate of water vapor passing through the wearing apparel product. by calculating, from the weighting and the reweighing steps.

2. The method of claim 1 wherein the wearing apparel is footwear.

3. The method of claim 1 or 2 wherein the liner material is microporous expanded polytetrafluorethylene.

* * * * *